US00PP21381P3

(12) United States Plant Patent
Vinson et al.

(10) Patent No.: US PP21,381 P3
(45) Date of Patent: Oct. 12, 2010

(54) STRAWBERRY PLANT NAMED 'EVES DELIGHT'

(50) Latin Name: ***Fragaria×ananassa* Duch.**
Varietal Denomination: Eves Delight

(75) Inventors: Peter Edward Vinson, Hernhill (GB); Simon Peter Warren, Hernhill (GB)

(73) Assignee: Edward Vinson Limited, Kent (GB)

( * ) Notice: Subject to any disclaimer, the term of this patent is extended or adjusted under 35 U.S.C. 154(b) by 0 days.

(21) Appl. No.: 12/320,140

(22) Filed: Jan. 21, 2009

(65) Prior Publication Data

US 2009/0229024 P1 Sep. 10, 2009

(30) Foreign Application Priority Data

Feb. 18, 2008 (EM) ..... PBR 2008/0369

(51) Int. Cl.
*A01H 5/00* (2006.01)

(52) U.S. Cl. ..... Plt./209

(58) Field of Classification Search ..... Plt./209, Plt./208

See application file for complete search history.

*Primary Examiner*—Kent L Bell
(74) *Attorney, Agent, or Firm*—Rosenberg, Klein & Lee

(57) ABSTRACT

This invention relates to a new and distinctive day-neutral cultivar, designated as 'Eves Delight' primarily adapted to the growing conditions in the United Kingdom. This day-neutral (everbearing) cultivar is primarily characterized by large flowers, an erect and upright growth habit, a large fruit size having superior uniformity, berries which are predominantly conical in shape with a small number of berries exhibiting a wedged shape, berries exhibiting a glossy bright red appearance, significantly better flavored berries, firmer fruit skin, significantly longer flower trusses, very moderate petiole pubescence, and a medium to late season production with moderate yields.

18 Drawing Sheets

Figure 1:
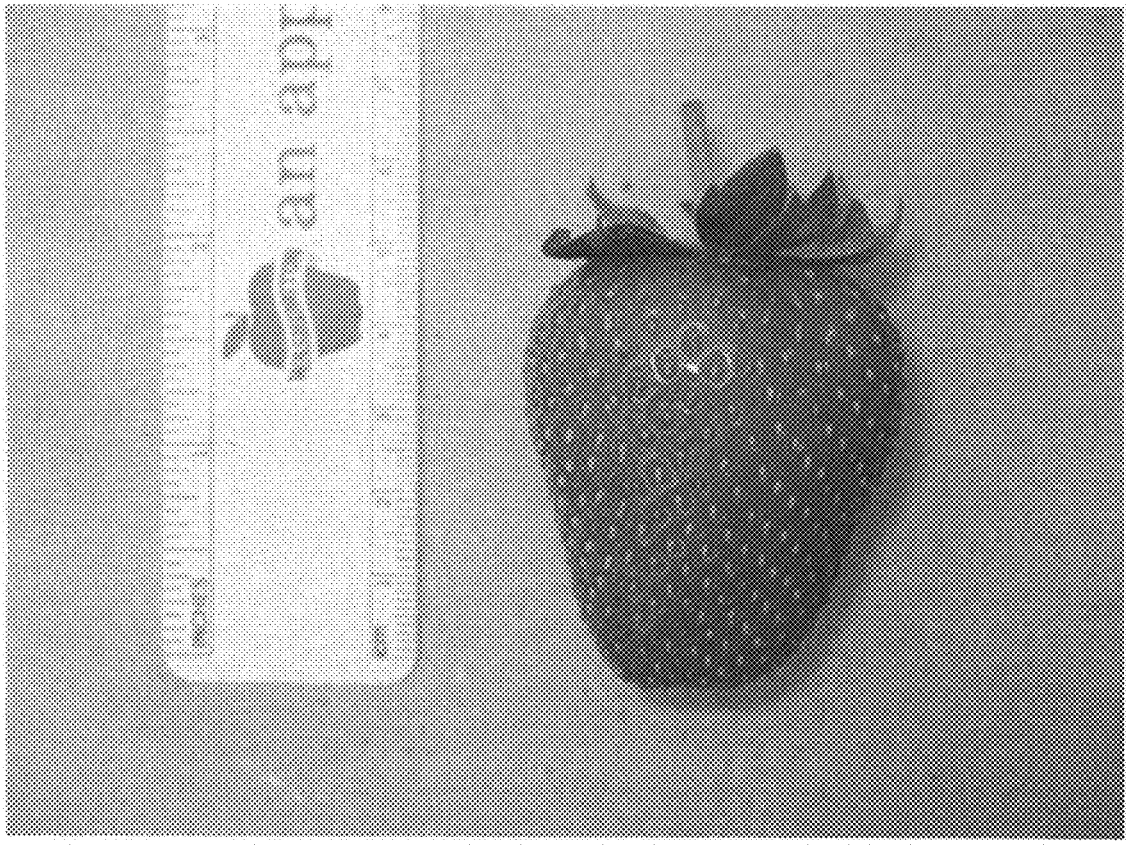

Genus and species: *Fragaria×ananassa* Duch.
Cultivar denomination: 'Eves Delight'.

BACKGROUND OF THE INVENTION

The new and distinct cultivar of strawberry originated from a controlled cross performed in a glasshouse as part of an ongoing breeding program in Kent, United Kingdom between the agricultural selections '02P78' (not patented) and '02EVA13R' (not patented) in 2003.

SUMMARY OF THE INVENTION

The present invention relates to a new and distinct day-neutral (everbearing) strawberry cultivar designated as 'Eves Delight'. The cultivar is botanically known as *Fragaria×ananassa* Duch. Under growing conditions in the United Kingdom this day-neutral (everbearing) cultivar has shown significant improvements over the variety 'Albion' (U.S. Plant Pat. No. 16,228). Improvements over 'Albion' include, but are not limited to, higher fruit quality, larger fruit size, superior eating quality and skin firmness, and paler fruit color.

The female parent, '02P78', is a day-neutral cultivar cropping in the United Kingdom in July August, and September. '02P78' is a low yielding, but high quality cultivar, expressing large fruit size. The fruit of '02P78' has a pale orange color, an even rounded shape, and good firmness characteristics. '02P78', however, exhibits a poor flavor.

The male parent, '02EVA13R', is a day-neutral cultivar cropping in the United Kingdom in July August, and September. '02EVA13R' is a low yielding cultivar expressing good fruit quality and size, however, the firmness and flavor of '02EVA13R' are below average.

The female parent, '02P78', is a hybrid of *Fragaria×ananassa* Duch and the male parent, '02EVA13R', was derived from an open pollinated seed of an unknown cultivar of *Fragaria×ananassa* Duch. Both parental cultivars were selected in 2002 from the same field, and while they were not considered to have commercial potential, both parental selections were retained as parental cultivars. Accordingly, 'Eves Delight' is of the species *Fragaria×ananassa* Duch.

The seedling fruited in the summer of 2004 at the seedling field located in Kent, United Kingdom was originally designated '04CF21', and subsequently named 'Eves Delight' for introduction. '04CF21' was selected because the cultivar produced a moderate yield of extremely high quality and good sized fruit. Additionally, the cultivar exhibited a firmness and flavor of outstanding merit combined with a unique and pleasing aroma.

'Eves Delight' was trialed in trial plots in Kent, United Kingdom during the years 2005, 2006, 2007 and 2008. During the period of trials 'Eves Delight' was reproduced asexually for four (4) successive years. For each trial year, asexual propagation of 'Eves Delight' was by means of stolons (runners) and took place at the glasshouse facility as part located in Kent, United Kingdom. Additionally, during the year 2007, however, a limited number of 'Eves Delight' plants were reproduced asexually by stolons at a propagation facility in Kent, United Kingdom. In all four (4) generations, plants were observed for trueness to type during the fruiting phase with no abnormalities being observed. Further propagation, at nurseries located at Faversham and Deal in Kent and Southampton in Hampshire, United Kingdom, was completed on a larger scale in 2008 using tissue culture plants as mother plants. This propagation demonstrated no obvious abnormalities in these plants. All propagules of 'Eves Delight' have been observed to be true to type in that during all asexual multiplication, the vegetative and fruit characteristics of the original plant have been maintained.

The new cultivar is primarily adapted to the climate and growing conditions of south eastern England and other regions of similar climate and day length. These regions provide the necessary winter temperatures required for it to produce a strong vigorous plant and to produce fruit in the summer harvest season from June through September, depending on location.

The following list of traits, in combination, defines the new cultivar as a unique cultivar distinguishable from other commercial varieties in the region:

- erect, upright growth habit;
- large fruit size having superior uniformity;
- predominantly conically shaped berries with a small number of berries exhibiting a wedged shape;
- berries exhibiting a glossy bright red appearance;
- significantly better flavored berries;
- significantly firmer fruit skin;
- significantly longer flower trusses, their relative position to the leaves being exposed and protruding to the sides of the plant and loaded with fruit;
- very moderate petiole pubescence;
- medium to late season production with moderate yields; and
- extended harvest season.

BRIEF DESCRIPTION OF THE PHOTOGRAPHS

The accompanying color photographs show typical specimens of the new cultivar, designated at various stages of development as nearly true as is possible to make in color reproductions. The depicted plant and plant parts were from the 2008 harvest season, approximately five (5) months after planting.

FIG. 1 Typical fully developed primary fruit, measured in length (cm).

Figure 2:
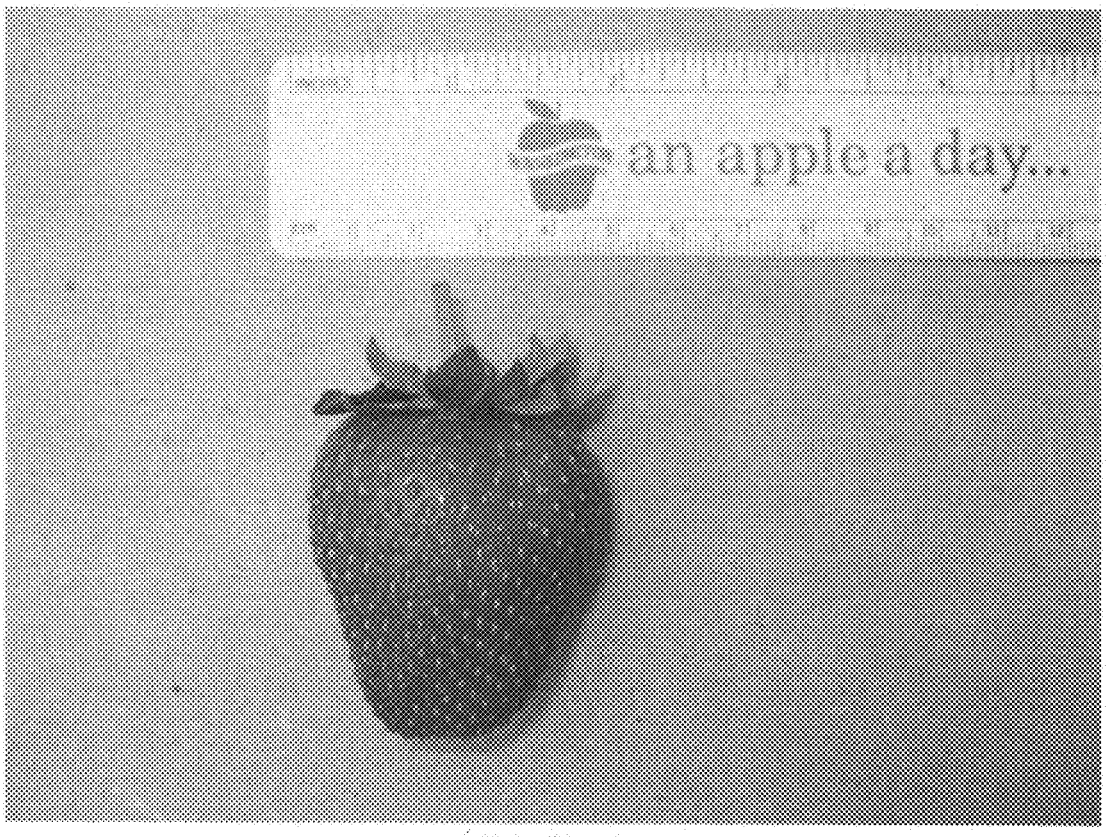

FIG. 2 Typical fully developed primary fruit, measured in width (cm).

Figure 3:
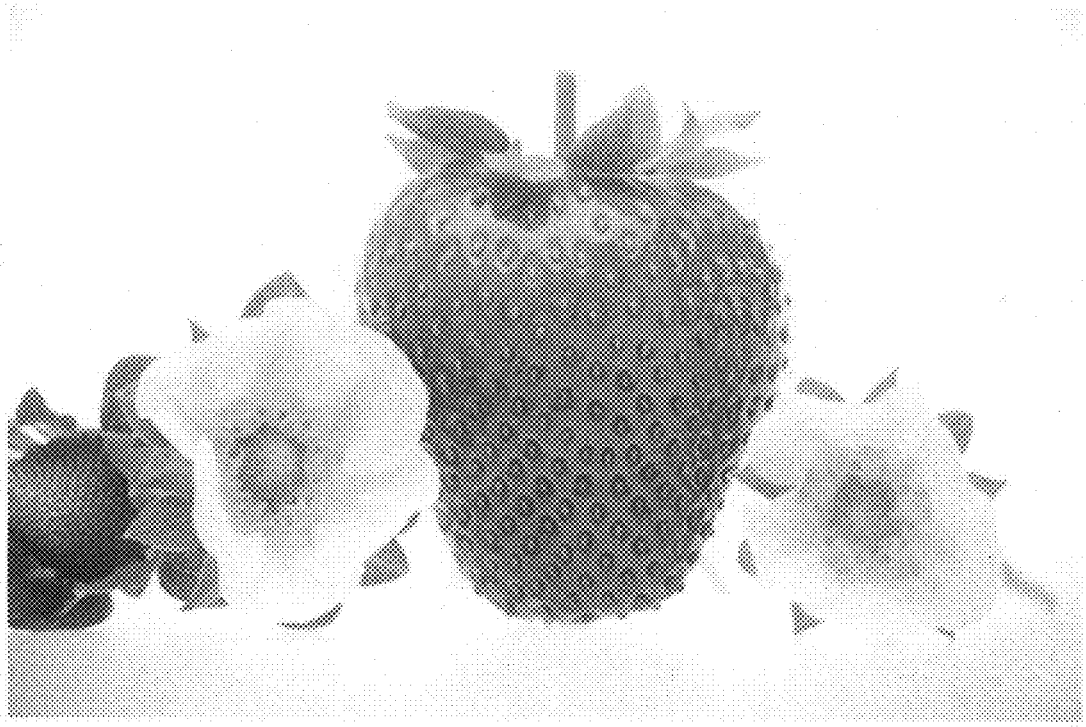

FIG. 3 Typical primary fruit and typical primary flowers.

Figure 4:
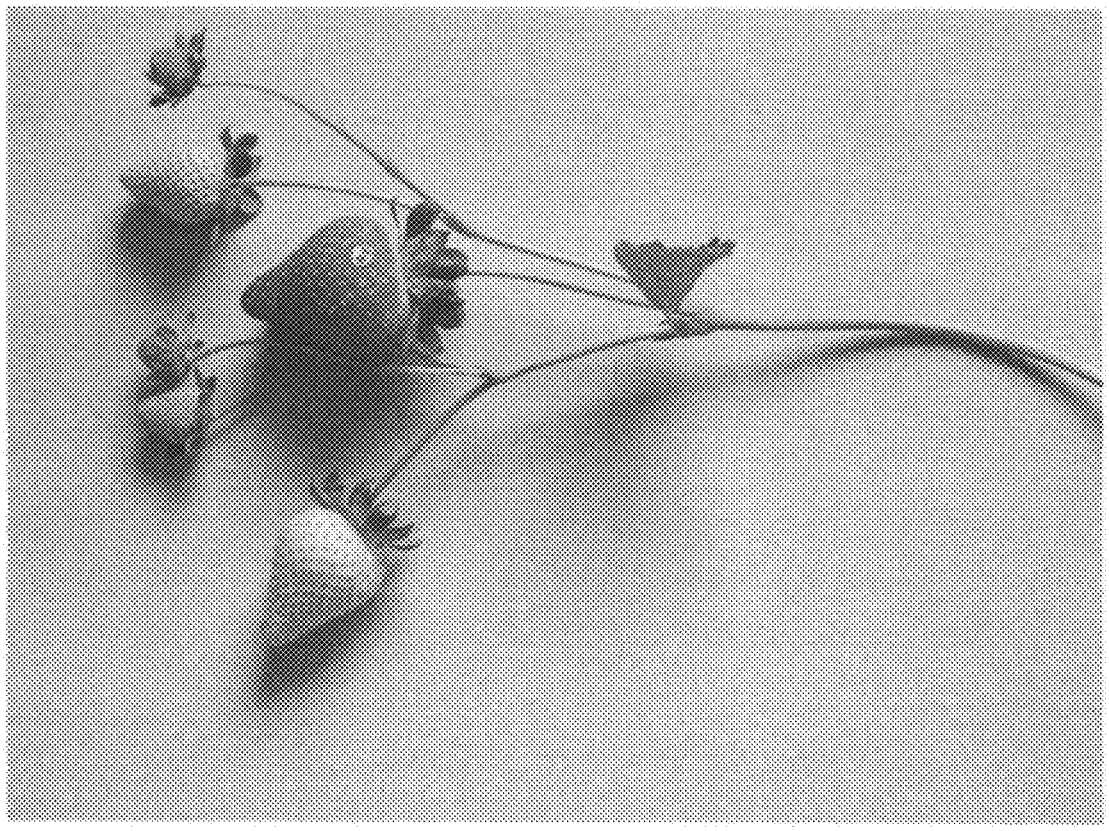

FIG. 4 Typical fruiting truss.

Figure 5:
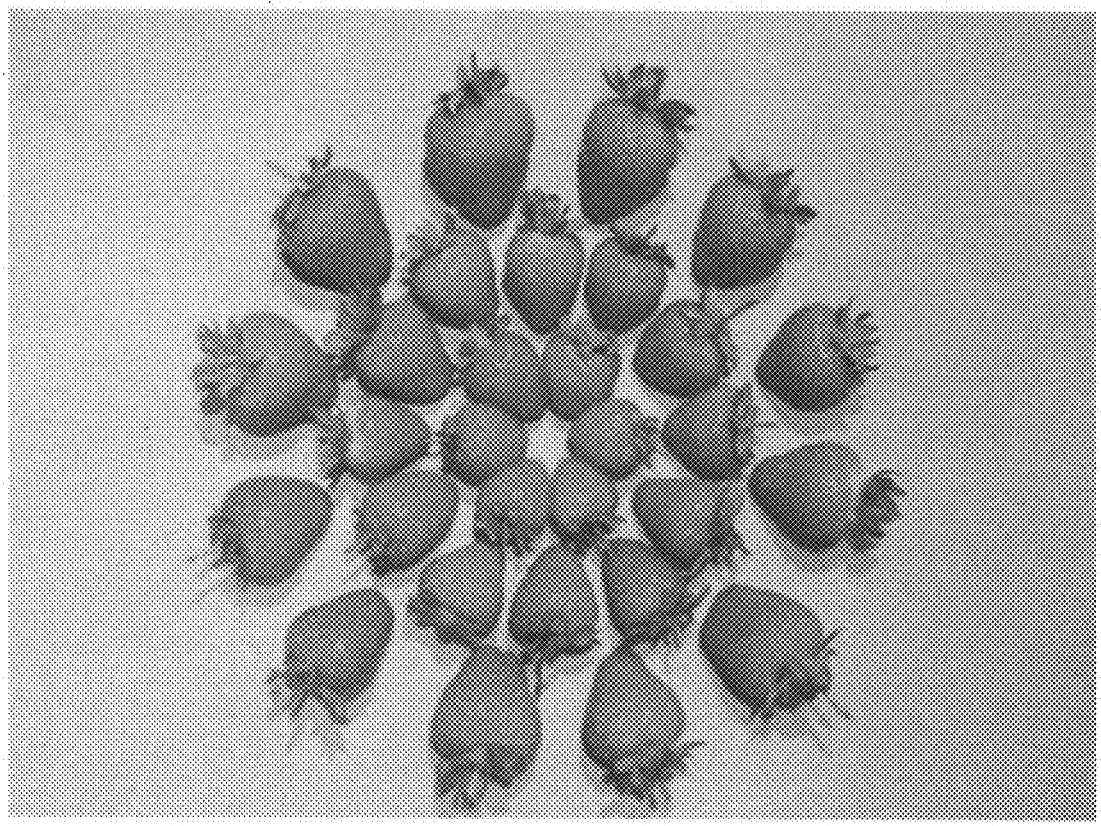

FIG. 5 A selection of large primary fruits (outer circle) having a wedge-shape, secondary fruits (middle circle) having a conical shape, and tertiary fruits (inner circle) having a rounded conical shape.

Figure 6:
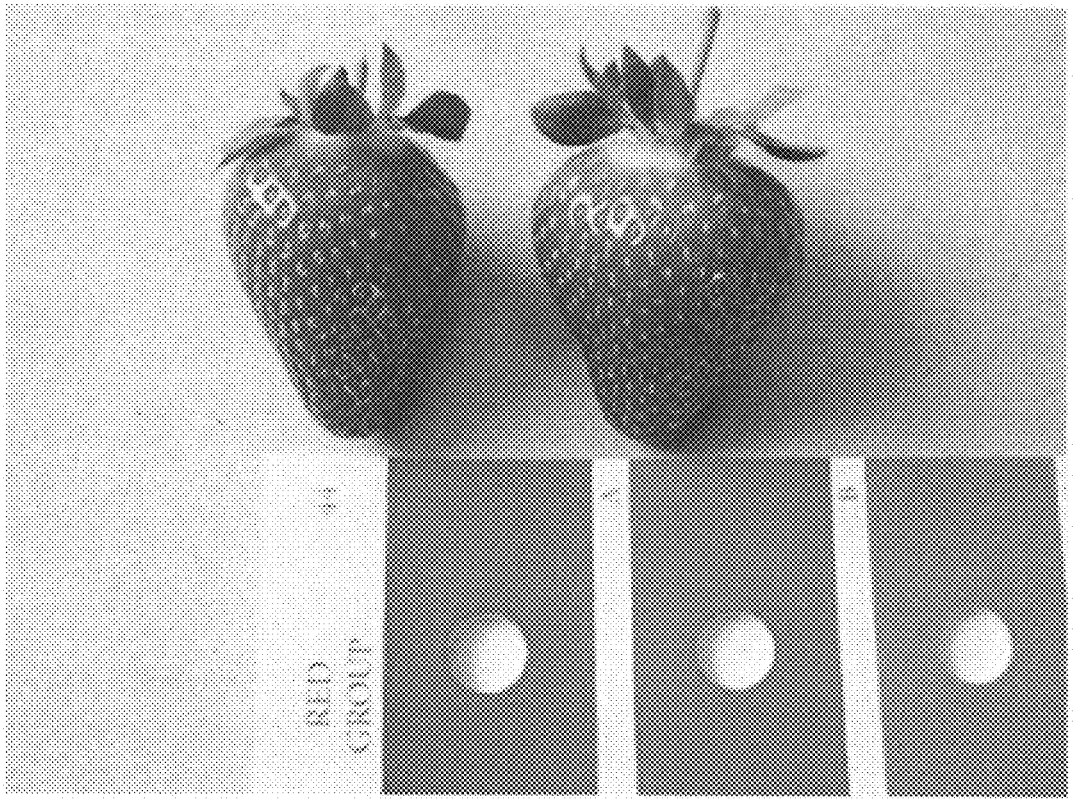

FIG. 6 'Eves Delight' fruit skin color identified using The Royal Horticultural Society Colour Chart (44 A).

Figure 7:
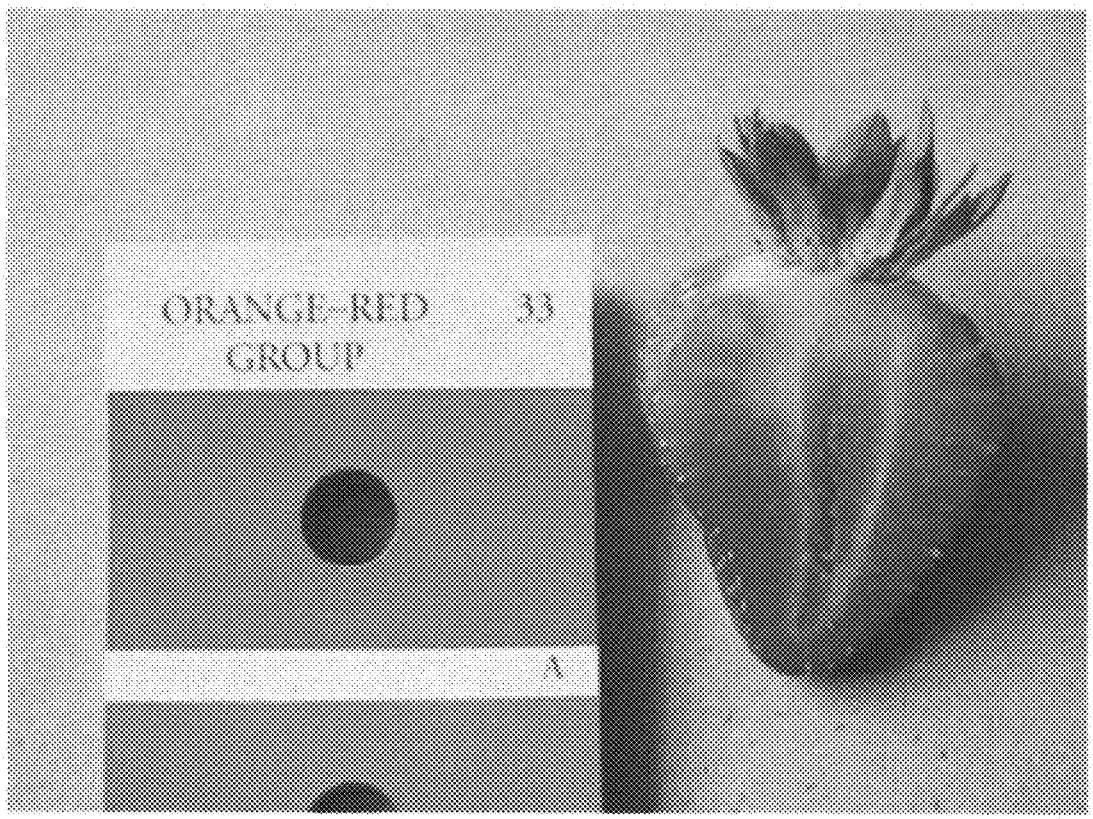

FIG. 7 Typical 'Eves Delight' fruit interior flesh coloration near the outside fruit surface identified using The Royal Horticultural Society Colour Chart (33 A).

Figure 8:
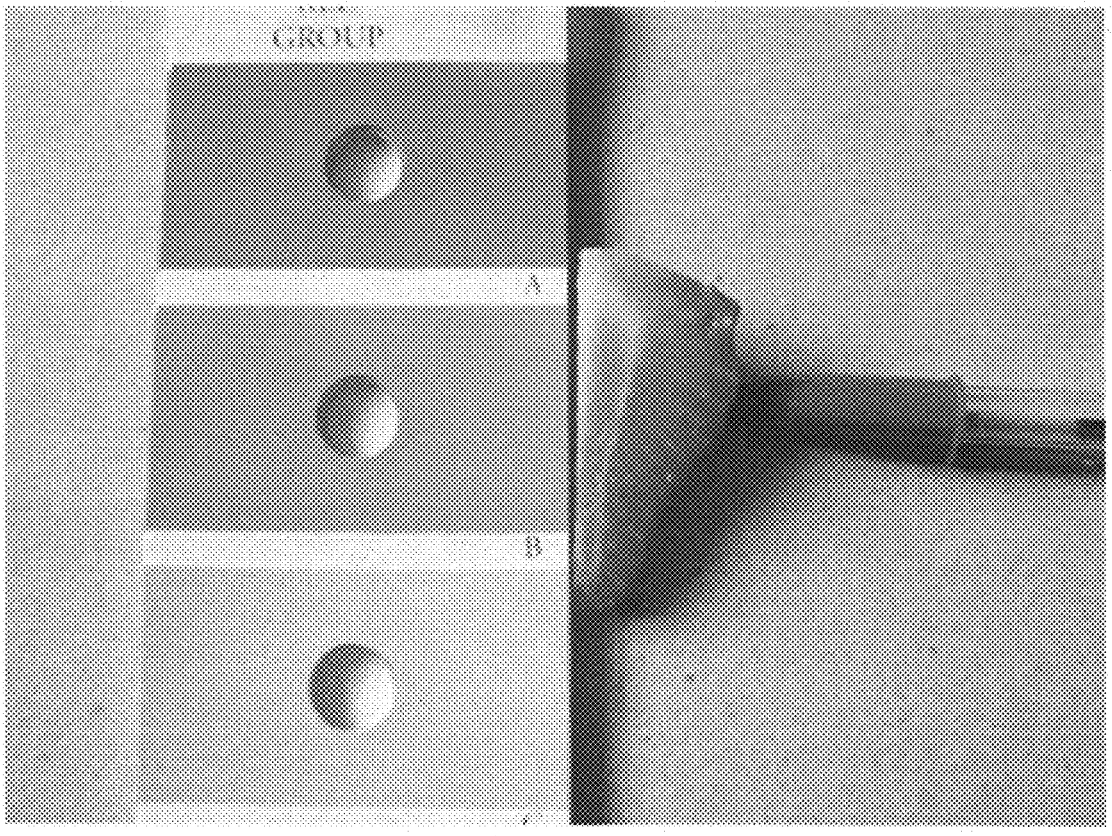

FIG. 8 Typical 'Eves Delight' fruit inner core coloration identified using The Royal Horticultural Society Colour Chart (39B).

Figure 9:
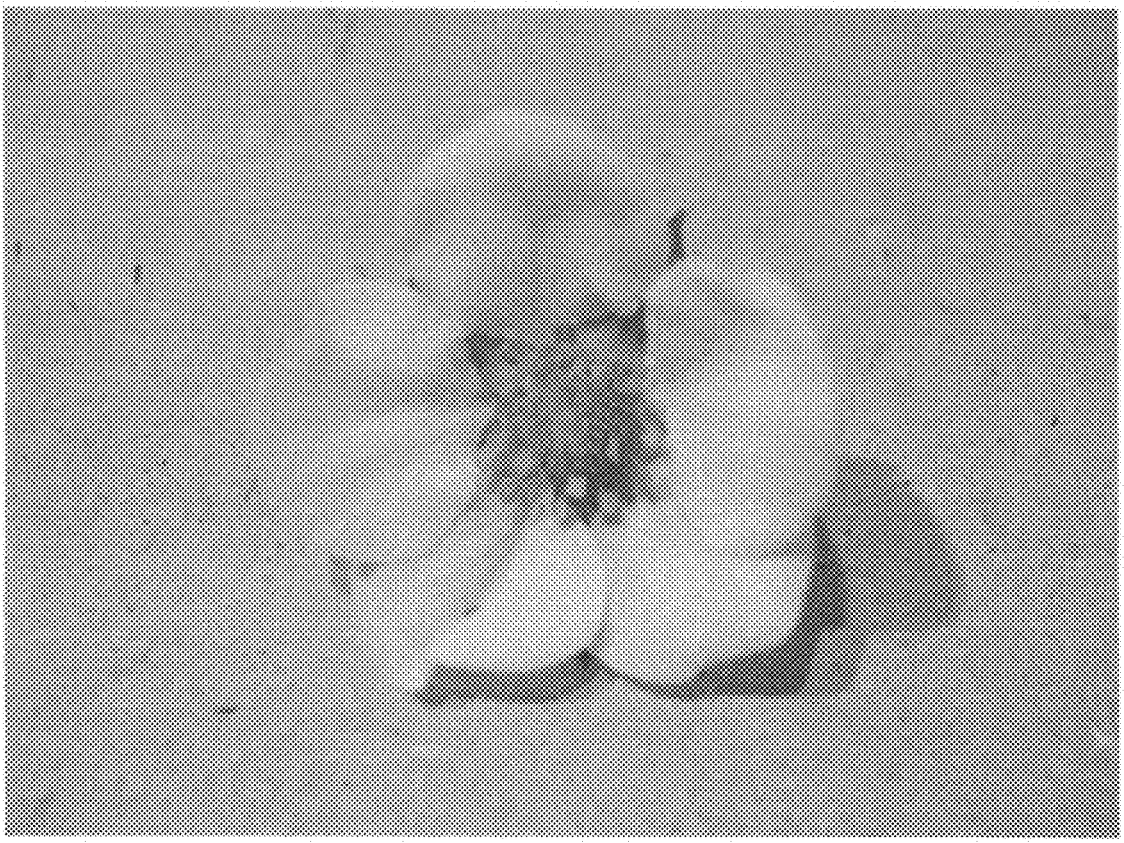

FIG. 9 An 'Eves Delight' flower with visible corolla (petals, stamens, and ovary).

Figure 10:
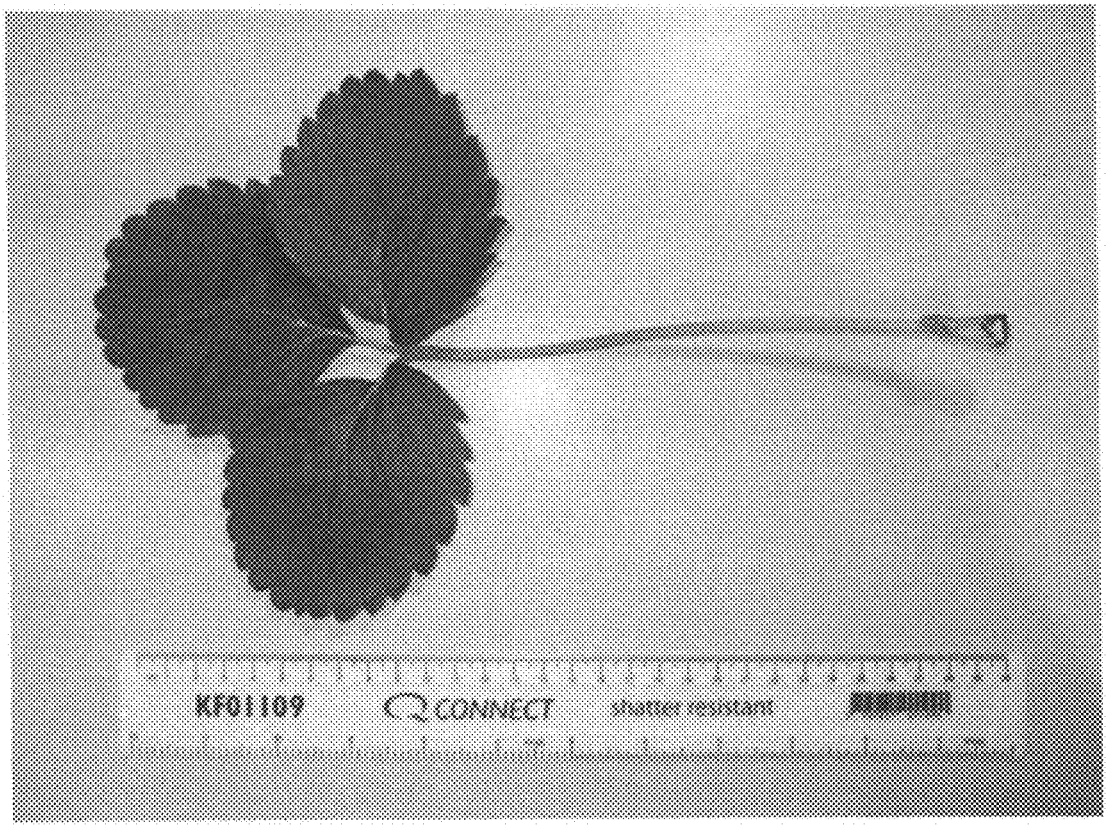

FIG. 10 A typical mature leaf with attached petiole and leafy stipule at the base of the petiole, measured in length and having rounded serrations and channel-like venations.

Figure 11:
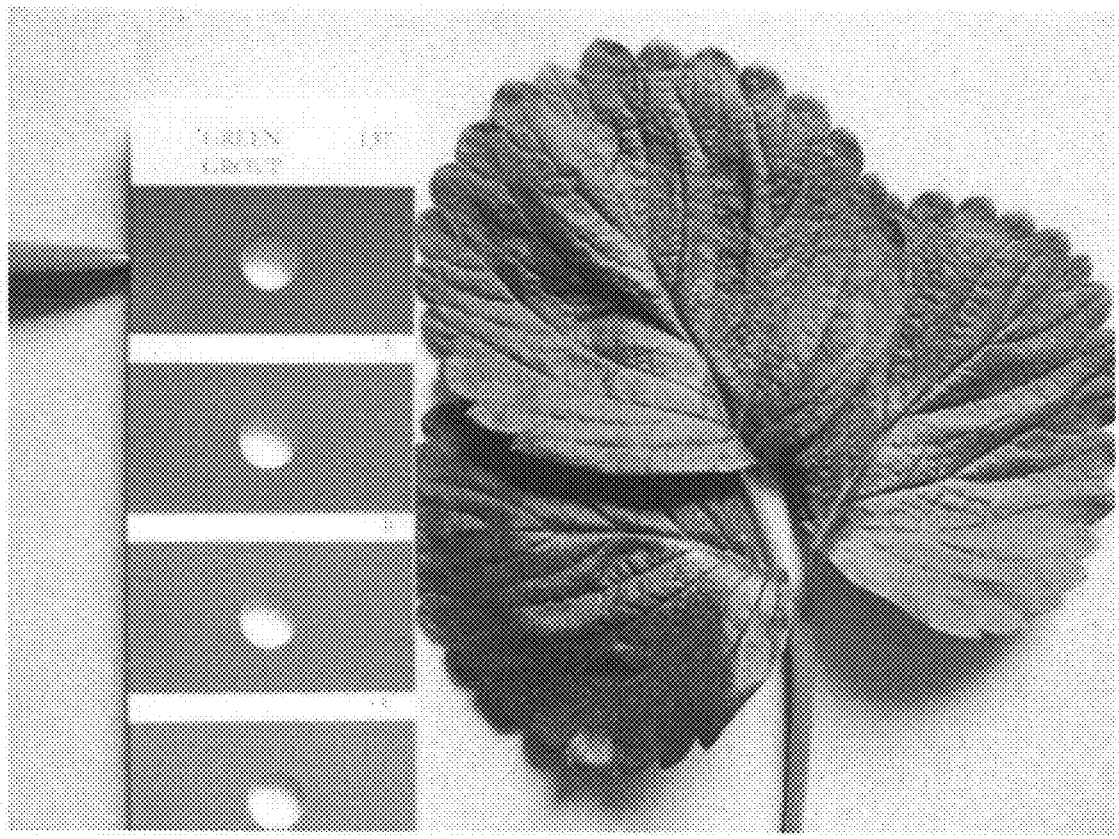

FIG. 11 Upper leaf surface color identification of a fully expanded 'Eves Delight' leaf using The Royal Horticultural Society Colour Chart (137A).

Figure 12:
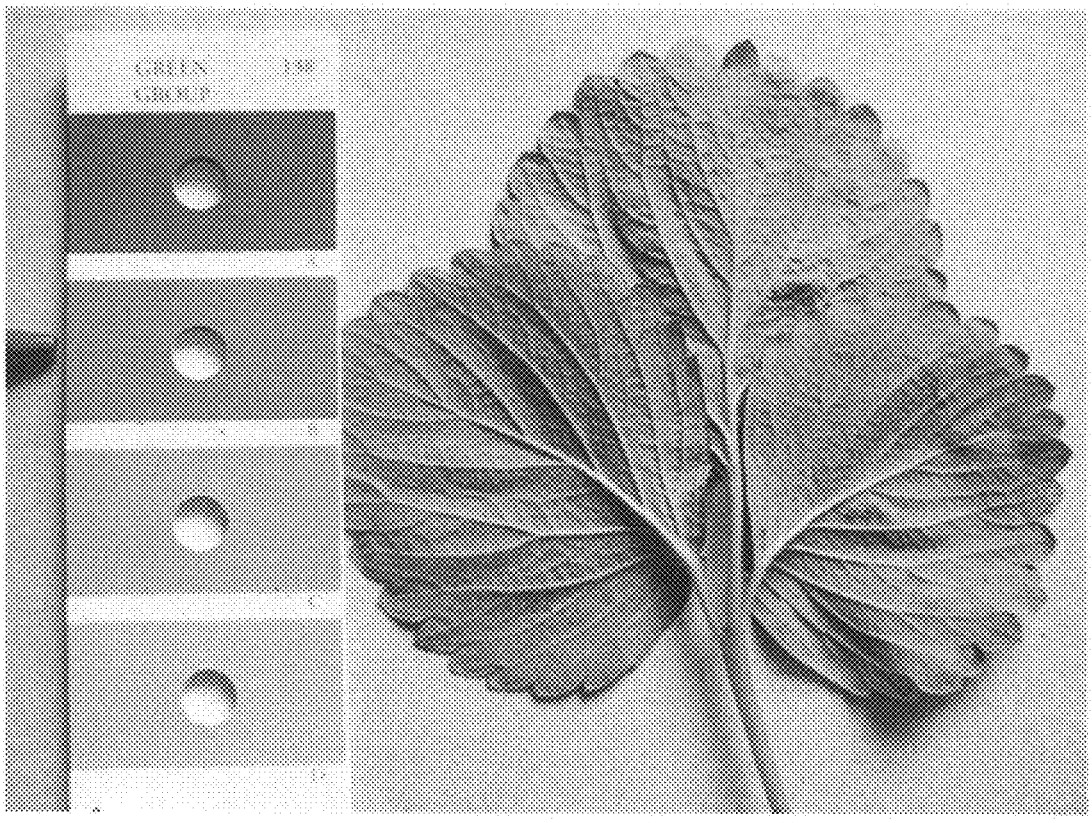

FIG. 12 Lower leaf surface color identification of a fully expanded 'Eves Delight' leaf using The Royal Horticultural Society Colour Chart (138B).

Figure 13:
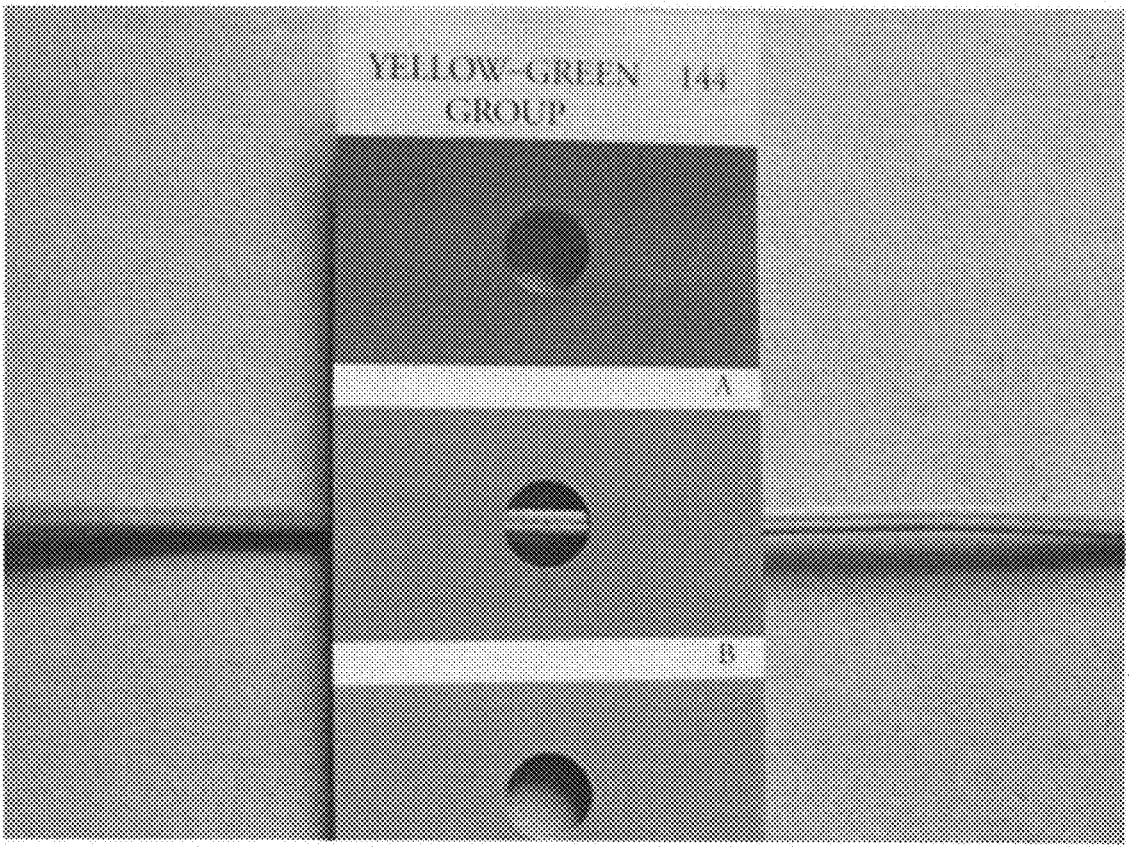

FIG. 13 Petiole color identification using The Royal Horticultural Society Colour Chart (144B).

Figure 14:
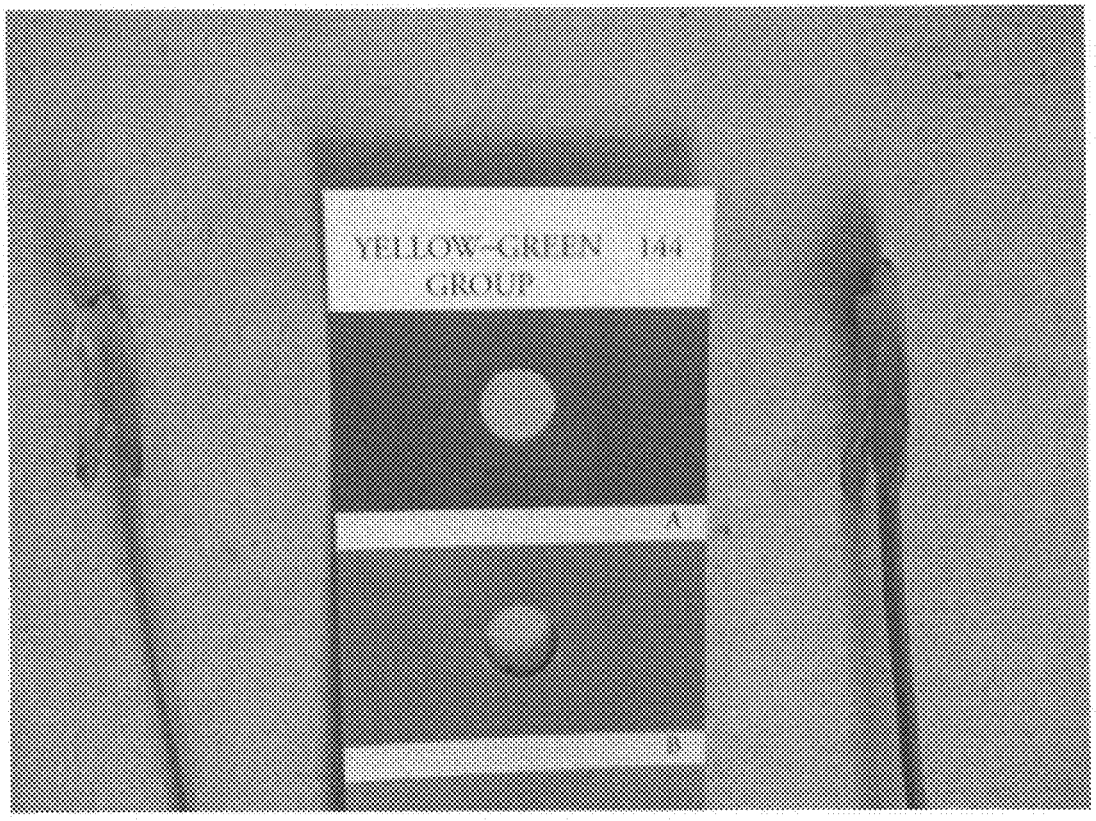

FIG. 14 Stipule color identification using The Royal Horticultural Society Colour Chart (144 A).

Figure 15:
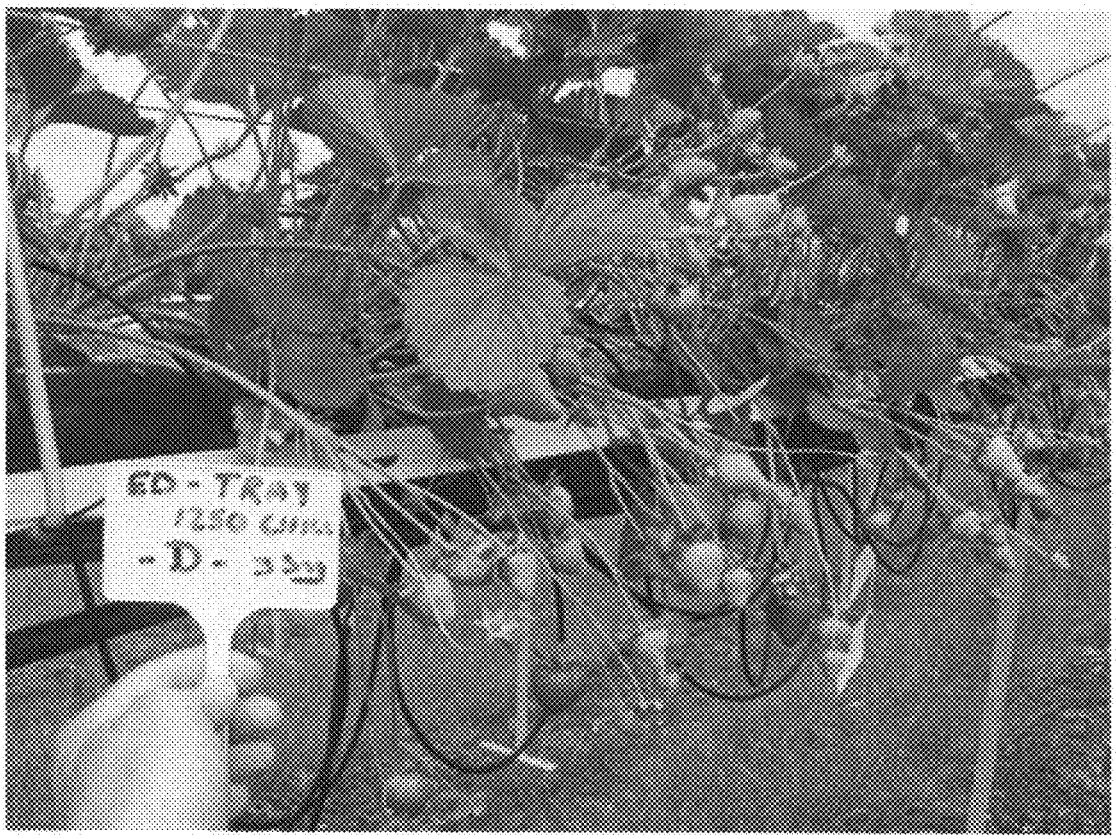

FIG. 15 Photo of a cropping 'Eves Delight' plant in midsummer with leaves, flowers, and fruits visible at various developmental stages.

Figure 16:
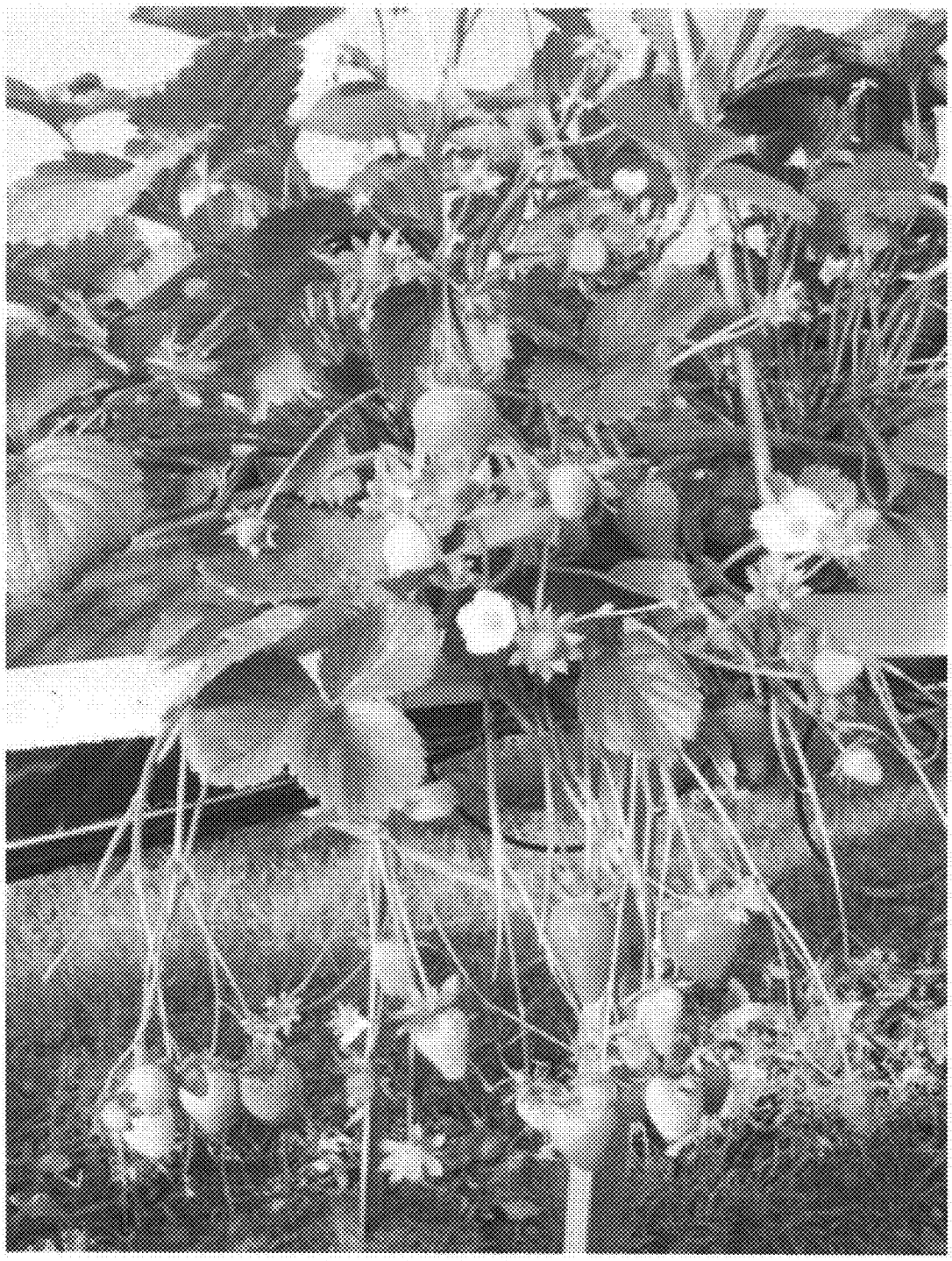

FIG. 16 Photo of a cropping 'Eves Delight' plant in late summer with leaves, flowers, and fruits visible at various developmental stages.

Figure 17:
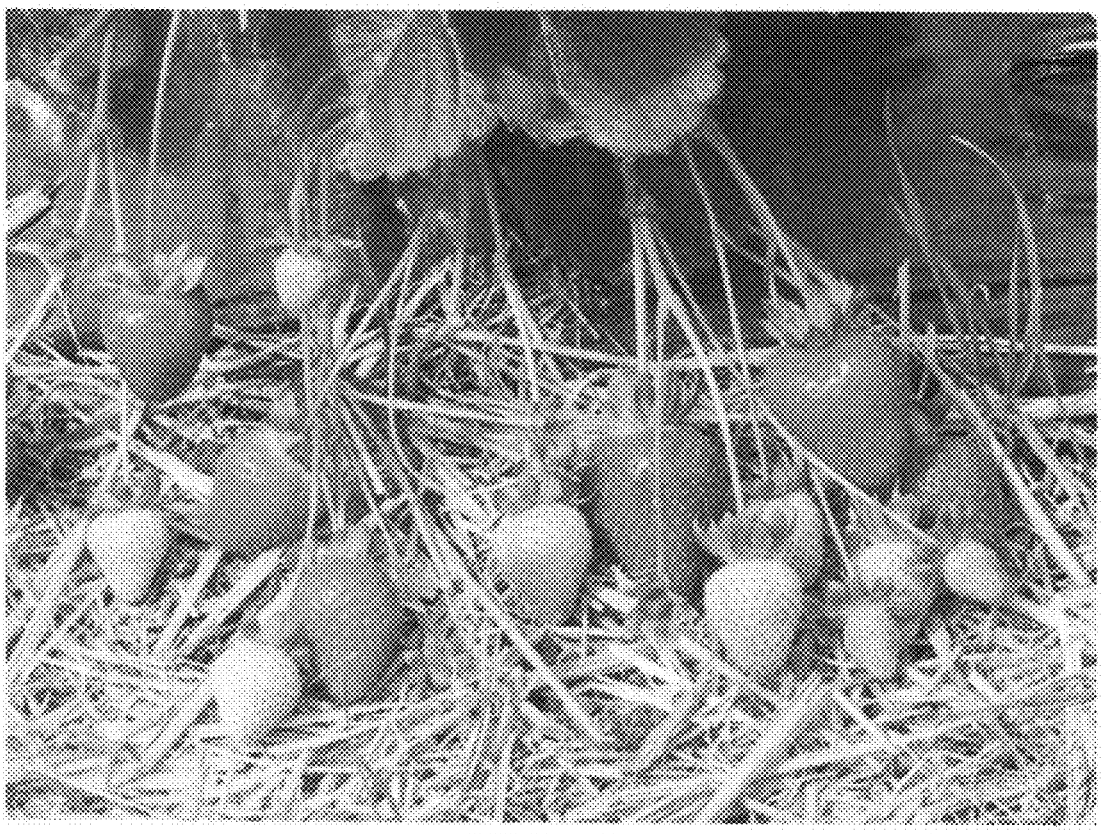

FIG. 17 Close shot of typical 'Eves Delight' fruit trusses showing large primary fruits as well as secondary and tertiary fruits.

Figure 18:
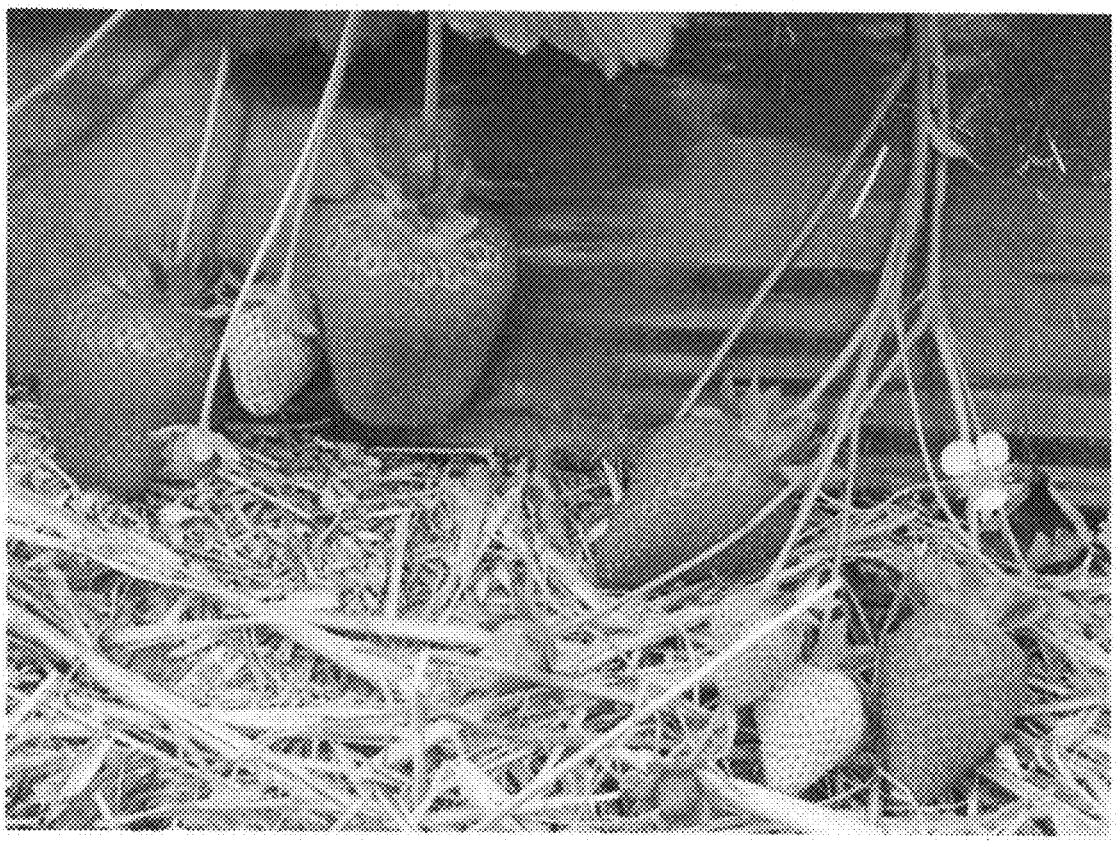

FIG. 18 Close shot of typical 'Eves Delight' fruit trusses with fruits at various developmental stage visible and an open flower on the same flower-fruit truss.

DETAILED BOTANICAL DESCRIPTION OF NEW CULTIVAR

The following description of 'Eves Delight', unless otherwise noted, is based on observations taken of plants and fruits grown in a trials field covered with tunnels and polyethylene covers as part of an ongoing breeding program in Kent, United Kingdom.

The following description is in accordance with UPOV terminology and the color terminology used herein is in accordance with The Royal Horticultural Society Colour Chart. The color descriptions and other phenotypical descriptions may deviate from the stated values and descriptions depending upon variation in environmental, seasonal, climatic, and cultural conditions.

Propagation

The new variety is principally propagated by way of stolons. Although propagation by stolons is presently preferred, other known methods of propagating strawberry plants may be used. Strawberry plants root well following transplanting.

Comparative Fruit Characteristics

The fruit characteristics of 'Eves Delight' include, but are not limited to, the characteristics of the fruit itself, the fruit production, and the fruit quality. Fruit characteristics for 'Eves Delight' were observed over four (4) seasons and the data was taken from the 2008 harvest season.

Table 1 shows the average fruit yield and size of 'Eves Delight' from measurements taken during the year 2008 when subjected to the environmental and growing conditions as they existed in the United Kingdom at that time. The measurements of 'Albion' were taken in the United States and cannot reflect the average total yields or primary berry weights of 'Albion' as they might exist under the same environmental or growing conditions that 'Eves Delight' was subjected to when grown in the United Kingdom.

In 2008 fruit harvest started on 6 June and continued through September. The plants of 'Eves Delight' were grown in a nursery in Kent, United Kingdom and planted in April 2008.

TABLE 1

Quantitative Comparison of 'Eves Delight' and 'Albion' Fruit Yields and Weights

| Cultivar (Average total yield in grams per plant) | Average | Cultivar (Primary berry weight in grams) | Average |
|---|---|---|---|
| 'Eves Delight' | 1,216 | 'Eves Delight' | 34.7 |
| 'Albion' | 2,417 | 'Albion' | 33.0 |

Table 2 compares the fruit characteristics of 'Eves Delight' berries with another standard variety. Measurements provided were taken from fully mature (ripe) primary fruits. Fruit width is measured across the widest part of the berry, typically, across the shoulders of the berry.

TABLE 2

Quantitative Comparison of 'Eves Delight' and 'Albion' Fruit Characteristics

| Characteristic | 'Eves Delight' | 'Albion' |
|---|---|---|
| Exterior Color | Red 44A (RHS) | 5R 3/7 (Munsell) |
| Internal Color (Inner Core) | Red 39B (RHS) | 7.5R 4/11 (Munsell) |
| Achene Color | Yellow 2A (RHS) | 7.5R 3/6 (Munsell) |
| Mature Fruit Length Mean (mm) | 51 | 60.6 |
| Mature Fruit Width Mean (mm) | 42 | 49.7 |
| Mature Fruit Length/ Width Ratio | 1.21 | 1.2 |
| Achenes per Primary Berry | 552/primary berry | 440.8/primary berry |
| Achene Position | Even to slightly protruded | Mostly indented, some even |

Table 3 compares the fruit quality characteristics of 'Eves Delight' with the fruit quality characteristics of 'Albion.' Comparisons of fruit quality include, but are not limited to, flesh firmness, soluble solids (as measured by % Brix), and acidity.

TABLE 3

Comparison of 'Eves Delight' and 'Albion' Fruit Quality Characteristics

| Characteristic | 'Eves Delight' | 'Albion' |
|---|---|---|
| Fruit Skin Firmness | Firm | Firm to very firm |
| Flesh Firmness | Soft internal texture | Firmer internal texture |
| Fruit Appearance | Bright red, high gloss | Dark red in color and low gloss |
| Fruit Aroma | Strong aroma | Medium aroma |
| Fruit Sweetness | High sugars, strong sweetness | Medium sweetness |
| Soluble Solids (% Brix) | 10.5% | 8.5% |
| Acidity | Low acidity | Medium acidity |

Detailed fruit characteristics of 'Eves Delight':

*Ratio of length to width.*—Longer than broad.

*Size.*—Large.

*Predominant shape.*—Conical.

*Aroma.*—Strong.

*Differences in shape between primary and secondary fruit.*—Moderate to strong.

*Differences in shape between primary and tertiary fruit.*—Slight to moderate.

*Band without achenes.*—Very small width.

*Color of mature fruit (ripe).*—Bright red (Red 44A).

*Evenness of color.*—Even.

*Glossiness.*—High.

*Achene position.*—Even to slightly protruded.

*Attitude of the calyx segments.*—Equally flush and reflexed.

*Color of the upper (adaxial) surface of the calyx.*—Green (Green 138A).

*Color of the lower (abaxial) surface of the calyx.*—Green (Green 143A).

*Size of calyx in relation to fruit diameter.*—Generally smaller.

*Firmness of skin.*—Very firm.

*Firmness of flesh.*—Moderate firmness.

*Color of flesh.*—Interior flesh coloration near the outside edges of the fruit surface approaches bright orange-red (Orange-Red 33A) and the inner core approaches red (Red 39B).

*Hollow center.*—Moderately expressed in primary fruit, weakly expressed in secondary and tertiary fruit.

*Achene color.*—Generally bright yellow (Yellow 2A), however, when fully exposed to light, achenes are red (Red 39A) in color.

*Time of flowering (50% of plants at first flower).*—Medium to late.

*Time of ripening (50% of plants with first ripe fruit).*—Medium to late.

*Type of bearing.*—Day-neutral (everbearing).

Comparative Plant Characteristics

Table 4 is a comparison of the plant characteristics of 'Eves Delight' with the plant characteristics of 'Albion' when the varieties were grown side-by side in Kent, United Kingdom. Comparisons of plant characteristics include differences in plant height, width, and breadth.

TABLE 4

Quantitative Comparison of 'Eves Delight' and 'Albion' Plant Characteristics

| Characteristic | 'Eves Delight' | 'Albion' |
|---|---|---|
| Plant Height Mean (mm) | 380 | 252 |
| Plant Width Mean (mm) | 427.5 | 388 |
| Plant Breadth Mean (mm) | 460 | 370 |

*Size.*—Large.

*Habit.*—Erect and open.

Comparative Foliage Characteristics

Table 5 compares the leaf characteristics of 'Eves Delight' with the leaf characteristics of 'Albion.' Foliage characteristics are taken from a fully mature tri-foliate leaf during mid-season.

TABLE 5

Quantitative Comparison of 'Eves Delight' and 'Albion' Plant Foliage Characteristics

| Characteristic | 'Eves Delight' | 'Albion' |
|---|---|---|
| Adaxial Surface Color | Green 137A (RHS) | 5GY 3/2 (Munsell) |
| Abaxial Surface Color | Green 138B (RHS) | 5GY 5/6 (Munsell) |
| Mid-tier Leaflet Length Mean (mm) | 92 | 73 |
| Mid-tier Leaflet Width Mean (mm) | 93 | 68 |
| Petiole Length Mean (mm) | 224 | 105 |
| Petiole Diameter (mm) | 4 | 4.1 |
| Petiole Color | Yellow-Green 144B (RHS) | 5GY 7/10 (Munsell) |
| Petiolule Length Mean (mm) | 14 | 7.4 |
| Stipule Length Mean (mm) | 29 | 23.3 |
| Stipule Color | Yellow-Green 144A (RHS) | 5GY 6/8 (Munsell) |
| Serrations per Leaf | 19.2 | 71.8 |
| Number of Leaflets/Leaf | 3 | 3 |
| Leaf Convexity | Some flat, some slightly concave | Some flat, most slightly concave |

Detailed foliage characteristics of 'Eves Delight':

*Leaf.*—Color of adaxial surface — Dark green (Green 137A). Color of abaxial surface — Light green to nearly gray green (Green 138B). Shape in cross section — Flat to slightly concave. Blistering — Slight to strong on the mid-tier leaflet. Number of leaflets/leaf—Three.

*Mid-tier leaflet.*—Length/width ratio — Wider than long. Shape of base — The terminal leaflet is nearly round, slightly wider than long, the two side leaflets are oblique. Shape of base — The terminal leaflet base is obtuse. Shape of leaflet apex — The leaflet apex is generally rounded with the occasional apex expressing a retuse shape. Shape of serrations — Crenate. Venation of leaflets — Pinnate.

*Petiole.*—Pubescence density — Moderate. Petiole color — Medium to light green (Yellow-Green 144B).

*Petiolule.*—Mean petiolule diameter — 0.81 cm. Petiolule color — Medium to light green (Yellow-Green 144C).

*Stipule.*—Mean stipule width — 0.6 cm. Stipule color — Medium to dark green (Yellow-Green 144A). Anthocyanin coloration of stipules — Medium to light pink (Red 56B).

*Attitude of hairs.*—Hairs are perpendicular to the petiole.

*Bract leaflets.*—Length of bract leaflets — 6.6 cm. Length of bract leaflets including petiole — 14.36 cm. Width of bract leaflets — 3.68 cm. Shape of bract leaflet — Elliptic. Shape of bract leaflet apex — Rounded. Shape of bract leaflet base — Attenuate to obtuse. Bract leaflet margins — Crenate. Color of adaxial bract leaflet surface — Green to dark green (Green 139A). Color of abaxial bract leaflet surface — Medium green to green (Green 138B). Frequency of bract leaflets — Bract leaflets are present on over 90% of flower trusses.

Comparative Flower and Inflorescence Characteristics

Table 6 compares the inflorescence and secondary flower characteristics of 'Eves Delight' with the inflorescence and secondary flower characteristics of 'Albion.'. Inflorescence characteristics are taken from a fully mature plant during full bloom. Flower characteristics are taken from a primary flower at full maturity.

TABLE 6

Quantitative Comparison of 'Eves Delight' and 'Albion' Inflorescence and Secondary Flower Characteristics

| Characteristic | 'Eves Delight' | 'Albion' |
|---|---|---|
| Fruiting Truss Length Mean (mm) | 218.2 | 170 |
| Corolla Diameter Mean (mm) | 36.8 | 27.0 |
| Calyx Diameter Mean (mm) | 37 | 35.8 |
| Petal Length Mean (mm) | 13.7 | 12.7 |
| Petal Width Mean (mm) | 14.7 | 12.6 |
| Petal Length/Width Ratio | 0.93 | 1.01 |
| Petals per Flower Mean | 5-6 | 5-8 |

Detailed inflorescence characteristics of 'Eves Delight':

*Position relative to foliage.*—Most exposed, some even.

*Mean fruiting truss diameter.*—0.48 cm.

*Fruiting truss color.*—Medium to dark green (Yellow-Green 144A).

Detailed flower characteristics of 'Eves Delight':

*Size of calyx relative to corolla.*—Equal.

*Corolla.*—Size — Large. Mean corolla width — 4.25 cm. Mean corolla depth — 0.8 cm. Petal length to width ratio — Wider than long. Petal shape — Nearly round having an obtuse base and apex. Petal margins — Entire. Color of adaxial petal surface — White (Green-White 157D). Color of abaxial petal surface — White (White 155D).

*Calyx.*—Sepal number — 11. Length of sepal — 1.6 cm. Width of sepal — 0.7 cm. Shape of sepal — Elliptic. Shape of sepal apex — Mostly acute, some caudate. Sepal margins — Entire. Color of adaxial sepal surface — Green to dark green (Green 137A). Color of abaxial sepal surface — Medium green to green (Green 138B).

Pest Reactions

The plants of 'Eves Delight' exhibit resistance to Powdery Mildew (*Podosphaera leucotricha*). They are also partially resistant to Crown Rot (*Phytophthora cactorum*) and Verticillium Wilt (*Verticillium* spp.). The susceptibility of the new cultivar to any of the virus complexes of the United Kingdom has not been determined.

COMPARISON WITH KNOWN VARIETIES

The variety which is believed to most closely resemble 'Eves Delight' is 'Albion' (U.S. Plant Pat. No. 16,228). When compared to similar cultivar 'Albion', 'Eves Delight' differs by the following characteristics.

'Eves Delight' is a typical day-neutral strawberry cultivar, being slightly weaker in expressing this character than 'Albion.' When compared to 'Albion' under United Kingdom growing conditions, 'Eves Delight' has a larger fruit size with greater uniformity and shape, a significantly firmer fruit skin, and a significantly longer flower truss. Additionally, the berries of 'Eves Delight' exhibit a glossy bright red appearance and are significantly better flavored than the berries of 'Albion.'

'Eves Delight' exhibits an erect, somewhat open growth habit. When 'Eves Delight' is grown in the United Kingdom, the plant size is generally greater than 'Albion.' Specifically, 'Eves Delight' exhibits longer petioles, larger leaves, and longer flower trusses. The leaf size of 'Eves Delight' is medium and the leaflets are generally round and slightly wider than longer than the leaflets of 'Albion.' Additionally, the petiole and petiolule length of 'Eves Delight' is significantly greater than 'Albion.' Petiole pubescence density of 'Eves Delight', however, tends to be very moderate compared to 'Albion' which exhibits a very heavy pubescence.

The leaflets of 'Eves Delight' typically exhibit a slightly round (obtuse) base and slightly rounded serrations. Moreover, 'Eves Delight' has a significantly smaller number of serrations per leaf than exhibited by 'Albion.' Some leaves of 'Eves Delight' exhibit slight to strong puckering/blistering, particularly on the mid-tier leaflet. Leaf pubescence is moderate, but less than that of 'Albion', and hairs appear perpendicular to the petiole.

Flower trusses typically grow clear of the foliage and flowers tend to open at or above the canopy, however, when the flower trusses are loaded with fruit, the trusses primarily protrude to the sides of the plant rather than in a completely upwards direction. Generally there are less flowers and fruit per truss than many other varieties, however, the number of flowers and fruit per truss is similar to Albion.

The flowers of 'Eves Delight' are slightly larger and stronger than those of 'Albion' and are generally fewer in numbers.

The primary flowers for 'Eves Delight' are noticeably larger than those of 'Albion' and 'Eves Delight' exhibits wider petals than 'Albion'. The calyx of 'Eves Delight' is distinctively larger than those of 'Albion.' The calyx on primary fruit for 'Eves Delight' exhibits some serration, a feature that is less common and/or visible on secondary and tertiary fruit.

The berries of 'Eves Delight' are large in size with a shape that is primarily wedge-shaped or conical. When grown in the United Kingdom, 'Eves Delight' fruit is less prone to ridging than 'Albion.' Moreover, the average number of achenes per primary berry of 'Eves Delight' is greater than the average number of achenes per primary berry of 'Albion'.

The external and internal fruit color of 'Eves Delight' is brighter and is substantially lighter than the color expressed by 'Albion.' At higher temperatures, the fruit of 'Eves Delight' appears to be unaffected and retains its bright red color. 'Albion' fruit, however, has a darker skin coloration that typically becomes darker when exposed to higher temperatures.

'Eves Delight' is significantly sweeter and juicier than 'Albion' throughout the cropping season, providing a very pleasant combination of flavor, sugar and acidity. The fruit flesh of 'Eves Delight' is less firm than that of 'Albion' providing for a less crunchy texture and a more pleasant eating experience. 'Eves Delight' retains a very good fruit quality throughout the cropping season and is stable in its essential characteristics, i.e. fruit size, shape, quality, color, firmness, Brix levels, and good plant habit.

Commercial ratings for 'Eves Delight' are better than that of 'Albion.' insomuch as 'Eves Delight' has significantly better qualities and a smaller fraction of non-marketable or class 2 fruit than 'Albion.'

When grown in the United Kingdom under appropriate management, 'Eves Delight' has larger fruit size than 'Albion', however, it produces slightly less yield per individual plant than 'Albion.' Flower initiation and flower expression of 'Eves Delight' are generally linear; however, variation in the climate might cause slight fluctuation. Termination of flowering is temperature dependent and day-length independent. 'Eves Delight' cropping season starts somewhat earlier than 'Albion' under United Kingdom growing conditions.

What is claimed is:

1. A new and distinct cultivar of strawberry plant named 'Eves Delight' substantially as herein described and illustrated by the characteristics set forth above.

* * * * *